United States Patent [19]

Burns

[11] Patent Number: 5,380,282
[45] Date of Patent: * Jan. 10, 1995

[54] BALLOON CATHETER ASSEMBLY

[75] Inventor: Matthew M. Burns, Orono, Minn.

[73] Assignee: SciMed Life Systems, Inc., Maple Grove, Minn.

[ * ] Notice: The portion of the term of this patent subsequent to Nov. 9, 2010 has been disclaimed.

[21] Appl. No.: 124,885

[22] Filed: Sep. 21, 1993

Related U.S. Application Data

[63] Continuation of Ser. No. 748,839, Aug. 23, 1991, Pat. No. 5,259,839.

[51] Int. Cl.⁶ ............................................. A61M 29/00
[52] U.S. Cl. ........................................ 604/96; 604/99; 606/194
[58] Field of Search ................ 606/192, 194; 604/96, 604/99, 101, 165

[56] References Cited

U.S. PATENT DOCUMENTS

| | | | |
|---|---|---|---|
| 3,402,717 | 9/1968 | Doherty | 128/351 |
| 3,675,658 | 7/1972 | Taylor | 128/349 |
| 3,707,151 | 12/1972 | Jackson | 128/351 |
| 3,726,283 | 4/1973 | Dye et al. | 128/349 |
| 4,085,757 | 4/1978 | Pevsner | 128/325 |
| 4,102,342 | 7/1978 | Akiyama et al. | 128/325 |
| 4,213,461 | 7/1980 | Pevsner | 128/348 |
| 4,456,000 | 6/1984 | Schjeldahl et al. | 128/1 |
| 4,509,523 | 4/1985 | Pevsner | 128/658 |
| 4,598,707 | 7/1986 | Agdanowski et al. | 128/207 |
| 4,606,347 | 8/1986 | Fogarty et al. | 128/344 |
| 4,646,742 | 3/1987 | Packard et al. | 128/344 |
| B1 4,762,129 | 7/1991 | Bonzel | 606/194 |
| 4,762,129 | 8/1988 | Bonzel | 128/344 |
| 4,782,834 | 11/1988 | Maguire et al. | 128/344 |
| 4,811,737 | 3/1989 | Rydell | 128/344 |
| 4,813,934 | 3/1989 | Engelson et al. | 604/99 |
| 4,819,637 | 4/1989 | Dormandy, Jr. et al. | 128/325 |
| 4,820,262 | 4/1989 | Finney | 604/8 |
| 4,820,349 | 4/1989 | Saab | 128/344 |
| 4,846,174 | 7/1989 | Willard et al. | 128/344 |
| 4,848,344 | 7/1989 | Sos et al. | 128/344 |
| 4,877,031 | 10/1989 | Conway et al. | 128/344 |
| 4,932,959 | 6/1990 | Horzewski et al. | 606/194 |
| 4,944,745 | 7/1990 | Sogard et al. | 604/194 |
| 5,032,113 | 7/1991 | Burns | 604/96 |
| 5,059,176 | 10/1991 | Winters | 604/96 |
| 5,061,273 | 10/1991 | Yock | 606/194 |
| 5,085,636 | 2/1992 | Burns | 604/99 |
| 5,100,385 | 3/1992 | Bromander | 604/99 |
| 5,102,390 | 4/1992 | Crittenden et al. | 604/96 |
| 5,178,608 | 1/1993 | Winters | 604/101 |
| 5,265,622 | 11/1993 | Barbere | 604/165 |

Primary Examiner—John D. Yasko
Assistant Examiner—Anthony Gutowski
Attorney, Agent, or Firm—Nawrocki, Rooney & Sivertson

[57] ABSTRACT

An angioplasty balloon catheter having a balloon carried at the distal end of a catheter shaft. The catheter shaft includes an inflation lumen by which the balloon is inflated and deflated. A guide wire passage extends through the balloon. A guide wire assembly extends through the catheter shaft, through guide wire passage, and out the distal end of the balloon. The guide wire assembly carries, near its distal end, a selectively radially expandable valve which is used to limit or block fluid flow between the shaft lumen and the patient's body during inflation and deflation of the balloon.

20 Claims, 3 Drawing Sheets

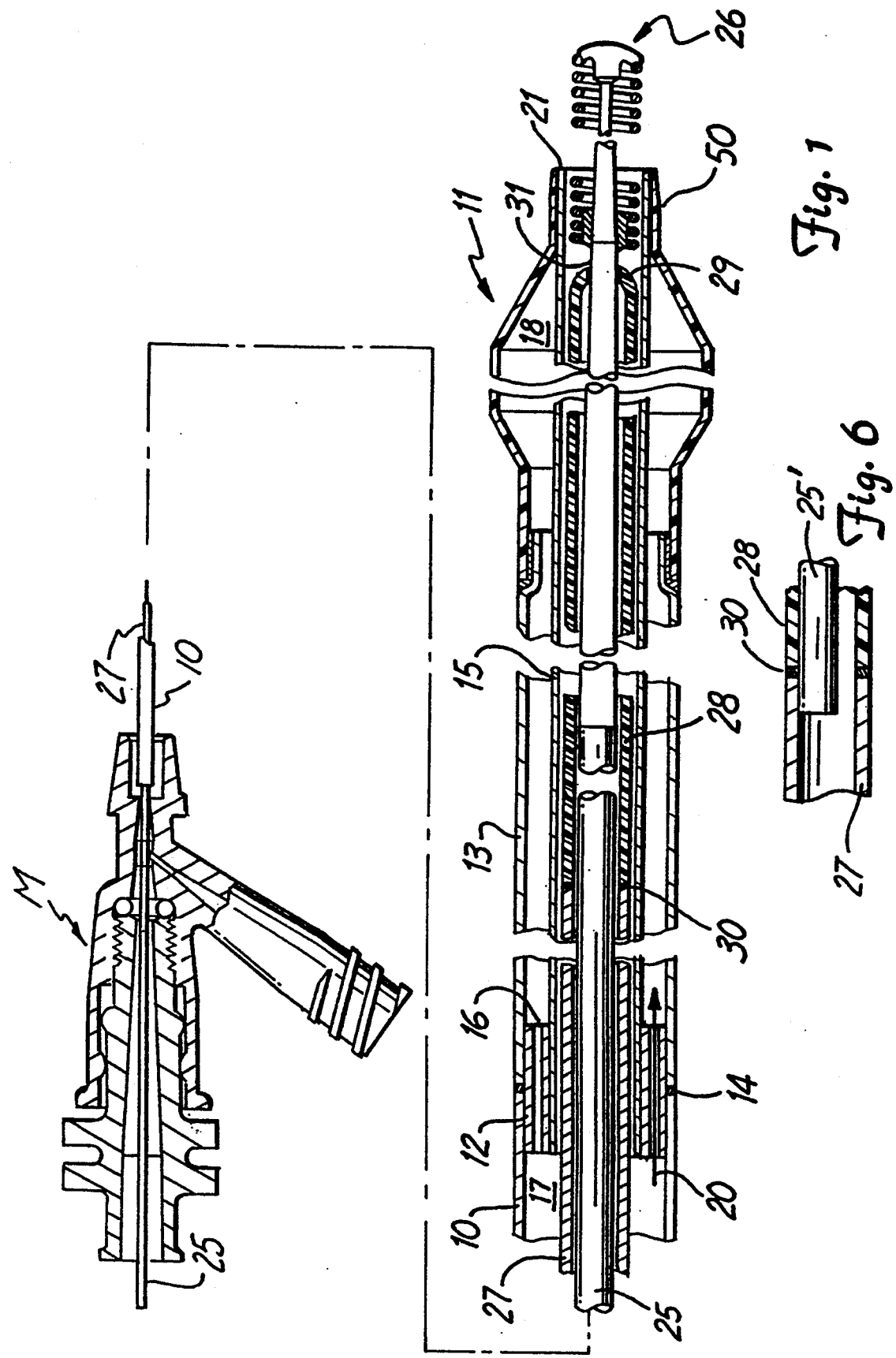

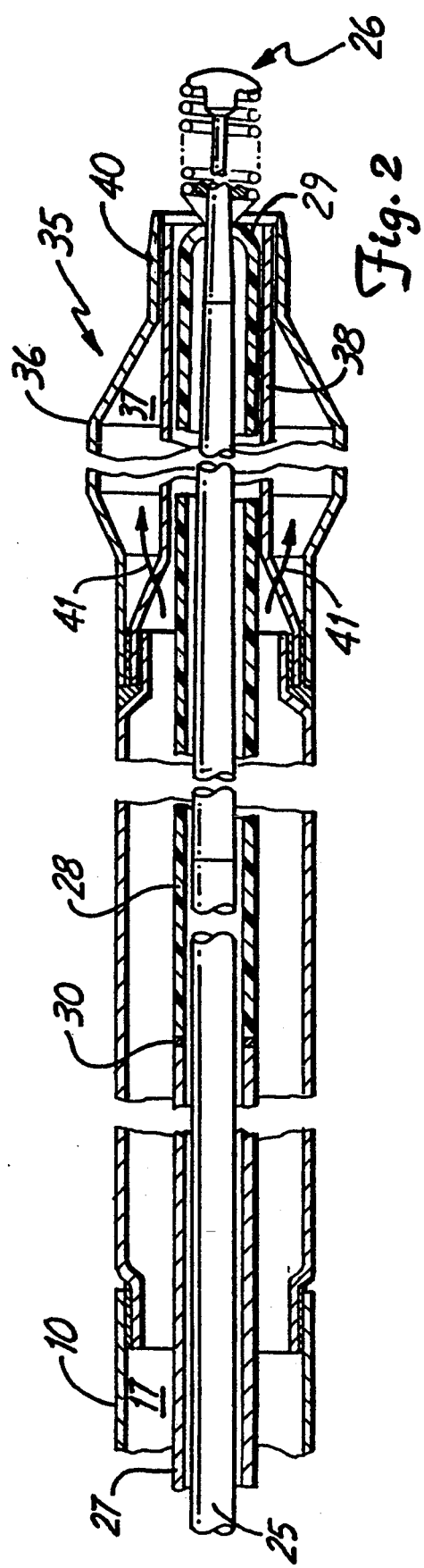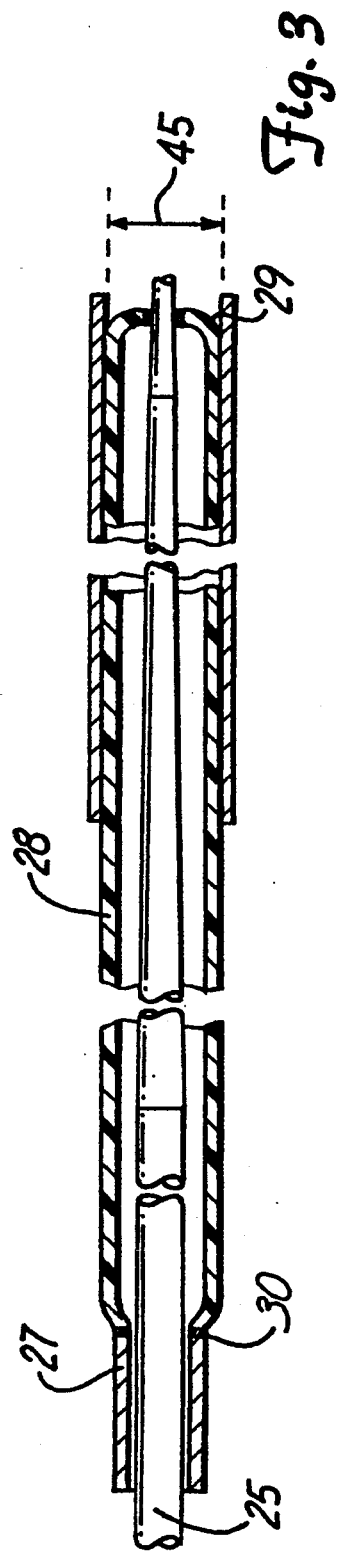

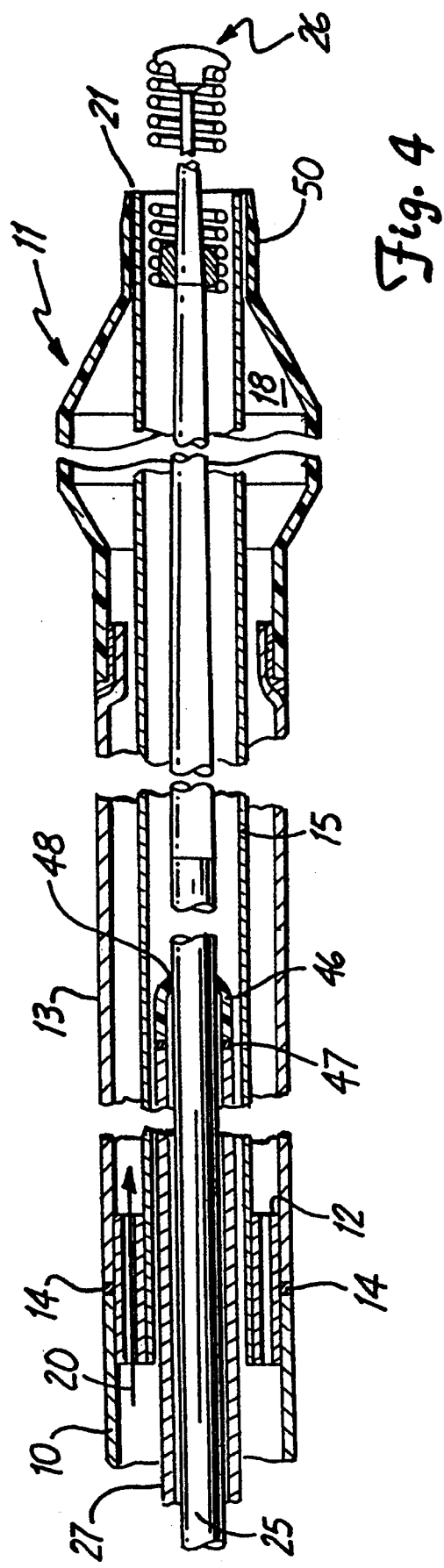
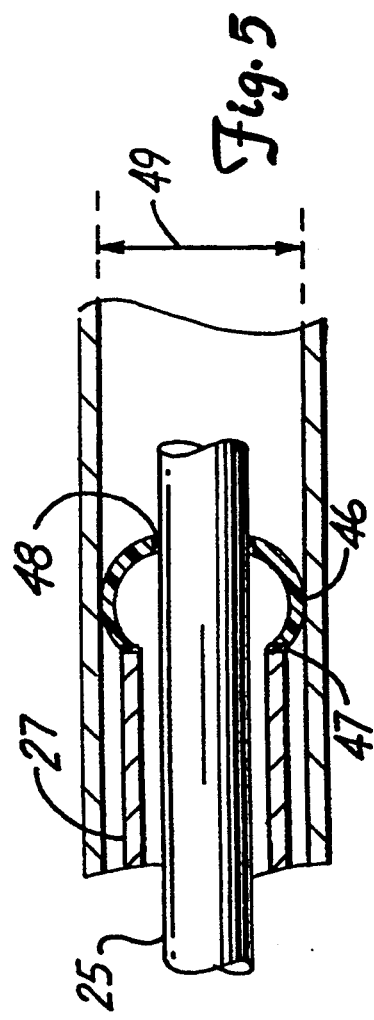

BALLOON CATHETER ASSEMBLY

This is a continuation of copending application Ser. No. 07/748,839 filed on Aug. 23, 1991, entitled "Balloon Catheter with Guidewire Valve", now U.S. Pat. No. 5,259,839, issued Nov. 9, 1993.

BACKGROUND OF THE INVENTION

The present invention relates to angioplasty and, in particular, to a dilatation balloon catheter.

Angioplasty has gained wide acceptance in recent years as an efficient and effective method for treating types of vascular diseases. In particular, angioplasty is widely used for opening stenoses in the coronary arteries. It is also used for treatment of stenoses in other parts of the vascular system.

A common form of angioplasty makes use of a dilatation catheter which has an inflatable balloon at its distal end. With the aid of fluoroscopy, a physician guides the catheter through the vascular system until the balloon is positioned across the stenosis. The balloon is then inflated by supplying fluid pressure through an inflation lumen to the balloon. Inflation of the balloon causes stretching of the artery and a pressing of the lesion into the artery wall to reestablish acceptable blood flow.

It is a common practice to employ a guide wire to establish the path to the stenosis. The dilatation catheter is then fed over the guide wire until the balloon is positioned within the stenosis. One advantage resulting from the use of a guide wire is the ability to maintain the desired position within the vascular system when replacing the catheter—as when a larger or smaller balloon is desired, for example. One disadvantage of many catheter systems employing a guide wire (often referred to as "over-the-wire" catheters), is the need to accommodate the guide wire within the catheter. This has often been accomplished through the provision of a guide wire lumen separate from that which delivers fluid pressure for balloon inflation/deflation. Such separate lumens result in larger catheter shaft diameters than are typical for fixed wire catheters.

In U.S. Pat. No. 5,032,113 by Matthew Burns issued Jul. 16, 1991, and in U.S. Pat. No. 5,035,705 by Matthew Burns issued Jul. 30, 1991, there are disclosed "innerless" over-the-wire catheters which feature a shaft with a single lumen for both inflation/deflation and the guide wire. The innerless catheters offer the advantages of an over-the-wire catheter without requiring a large diameter shaft. The disclosures of these two commonly-owned patents are hereby incorporated by reference.

SUMMARY OF THE INVENTION

The present invention is a balloon catheter assembly in which an inflatable balloon is carried at the distal end of a shaft, and in which a guide wire passage extends through the balloon. The shaft has a lumen which is used for inflation and deflation of the balloon and as a passageway for a guide wire. The guide wire extends through the shaft lumen, through the guide wire passage, and out the distal end of the balloon. The guide wire carries a radially expandable value member which can be expanded to restrict fluid flow through the guide wire passage during inflation and deflation of the balloon. When the valve member is not expanded, the guide wire is able to slide freely in an axial direction with respect to the catheter.

In preferred embodiments, the guide wire is formed by an elongated tube having a wire extending from the distal end thereof. The radially expandable valve member is carried at the distal end of the tube for expansion within an appropriate portion of the guide wire passage for the purpose of blocking fluid flow. The radially expandable valve member may be expanded for example, by internal fluid pressure or by relative axial movement of the tube and guide wire.

BRIEF DESCRIPTION OF THE DRAWINGS

FIG. 1 is a sectional view of a first preferred embodiment of a portion of a balloon catheter of the present invention, with the guide wire valve collapsed.

FIG. 2 is a sectional view of a second preferred embodiment of a portion of a balloon catheter of the present invention, with the guide wire valve collapsed.

FIG. 3 shows the guide wire valve of FIGS. 1 and 2 in its expanded state.

FIG. 4 is a sectional view of a third preferred embodiment of a balloon catheter with the guide wire valve collapsed.

FIG. 5 shows the guide wire valve of FIG. 4 in its expanded state.

FIG. 6 is a sectional view showing a portion of yet another guide wire assembly in accordance with the present invention.

DETAILED DESCRIPTION OF THE PREFERRED EMBODIMENTS

An over-the-wire catheter necessarily requires a passage for the guide wire and typically includes an opening at the distal end of the catheter assembly. The distal opening has the potential for fluid communication between the patient's body and catheter interior. When the guide wire extends through a dedicated guide wire lumen which is not in fluid communication with the balloon interior, this opening poses little difficulty. However, when the shaft lumen which is used for inflation/deflation of the balloon also functions as a guide wire lumen, a restriction of fluid flow between the catheter assembly and the body is at least desirable, if not necessary. The present invention provides the restricted flow through the provision of a guide wire which carries a radially expandable valve member. The expandable valve member may be deformable by internal pressure or by mechanical manipulation, or by both.

FIG. 1 is a sectional view showing the distal end of an innerless, over-the-wire, dilatation balloon catheter, which includes a portion of catheter shaft 10 and balloon assembly 11. Annular insert 12 is positioned within the distal end of shaft 10, while shaft extension 13 extends between shaft 10 and balloon assembly 11. Shaft 10 and shaft extension 13 are sealingly secured to each other at joint 14 in any known manner, as by adhesive bonding, for example. Inner tube 15 extends from insert 12 and through balloon 11 to define a guide wire passage through interior 18 of balloon 11. A series of ports 16 in insert 12 provide fluid communication between lumen 17 of shaft 10 and the interior 18 of balloon 11 through the annular path between the inner wall of shaft extension 13 and the outer wall of inner tube 15. Fluid flow through insert 16 is represented in FIG. 1 by arrow 20.

FIG. 1 also shows the proximal end of the dilatation catheter, which includes manifold M connected to the proximal end of shaft 10. For convenience of illustration, the proximal end of the catheter is shown in a smaller scale than the distal end.

That portion of the catheter described to this point is disclosed in U.S. Pat. No. 5,032,113. In essence, in the embodiment of FIG. 1, the balloon catheter, exclusive of the guide wire, includes a shaft 10 having a combination inflation guide wire lumen 17 by which balloon 11 is inflated and deflated via fluid communication through ports 16 and the passage between insert 12 and balloon interior 18 formed between shaft extension 13 and inner tube 15. For the purposes of the present invention, insert 16 may be positioned anywhere in shaft 10 or shaft extension 13. Also, shaft extension 13 may be eliminated with balloon 11 being secured directly to shaft 10.

The innerless catheter of U.S. Pat. No. 5,032,113 relies on the flow resistance through the guide wire passage defined by the inner dimensions of the inner tube (with a guide wire in place within that passage), for inflation and deflation of the balloon via control of the pressure in the shaft lumen. That is, with the guide wire in place in the guide wire passage of the inner tube, the flow resistance through the inner tube is sufficiently greater than the flow resistance between the shaft lumen and the interior of the balloon that the balloon may be inflated and deflated without undue passage of fluids between the shaft lumen and the patient's body through the distal end of the inner tube.

The present invention may similarly rely on such flow resistance, but provides a positive control of fluid flow through inner tube 15 by the provision of a guide wire which carries a selectively radially expandable valve member. Such a guide wire assembly is illustrated in FIG. 1 extending through lumen 17 of shaft 10 and through and from inner tube 15 at distal end 21 of the balloon 11. The guide wire assembly includes an inner wire element 25, which is referred to herein as a "guide wire" in that it may be constructed as a guide wire of conventional design, including a distal terminating tip assembly designated generally at 26. Surrounding guide wire 25 is an elongated tube 27. Carried at and extending from the end of the tube 27 is an elongated resilient valve member 28 which extends over a length of guide wire 25 and has a generally hemispherical terminus 29 with an aperture through which guide wire 25 extends. Valve member 28 is sealed to tube 27 at its proximal end, as by bond 30, and to guide wire 25 by bond 31. The interior of valve member 28 is in fluid communication with the interior of tube 27 such that a pressure induced in the interior of tube 27 will be communicated to the interior of valve member 28, which allows valve member 28 to be expanded by internal pressure. Expansion of valve member 28 causes its outer wall to extend from the configuration illustrated in FIG. 1 into contact with the inner wall of inner tube 15, thereby providing a positive valving action and a positive control of fluid flow through inner tube 15. Alternatively, or additionally, resilient valve member 28 may be expanded by a relative manipulation between guide wire 25 and tube 27. That is, maintaining tube 27 stationery while pulling guide wire 25 in an axial direction away from the distal end of the catheter will cause a longitudinal contraction of the valve member 28 and a corresponding radial expansion against the inner wall of inner tube 15. Either or both of these expansion techniques may be employed to provide a positive valving action within the guide wire passage of inner tube 15. Since this action takes place independently of the fluid communication between lumen 17 and balloon interior 18, it does not interfere with inflation/deflation of balloon 11.

The guide wire assembly may be constructed of any known and suitable materials. As indicated, the guide wire 25 may be of known construction. Tube 27 may be formed of a suitable stainless steel, while valve member 28 may be formed, for example, of a silicone rubber or latex. Tube 27 and guide wire 25 extend through and out the proximal end of the catheter shaft 10, thereby allowing pressure control within tube 27, and accordingly, within the interior of valve member 28, as well as to allow relative manipulation between guide wire 25 and tube 27. For the latter, it is likely necessary that guide wire 25 extend proximally beyond tube 27. Also, it may be desirable to reduce the diameter of the proximal portion of guide wire 25 from typical present guide wire dimensions such that the outside diameter of tube 27 may approximate those dimensions.

FIG. 2 illustrates an alternative balloon catheter with which the guide wire assembly of FIG. 1 may be employed. Throughout the Figures, like reference numerals designate like elements. In FIG. 2, balloon assembly 35 is formed of a balloon member 36 whose interior 37 is defined by a director 38. A balloon assembly construction of the type illustrated in FIG. 2 is disclosed in U.S. Pat. No. 5,035,705. As illustrated in FIG. 2, balloon member 36 and director 38 (which is permeable or includes at least one port therethrough for the passage of inflation fluid) join at a generally cylindrical segment 40 at the distal end of the catheter assembly. The intended inflation/deflation flow through director 38 is illustrated by the arrows 41. As can be seen, director 38 acts as an extension of lumen 17 for passage of the guide wire assembly with the cooperation between director 38 and valve member 28 acting to positively control the flow of fluids at least at segment 40 of the guide wire passage.

FIG. 3 illustrates a preferred embodiment of a guide wire assembly in accordance with the present invention with valve member 28 in its radially expanded state. In a relaxed state, valve member 28 is generally tubular with an outer diameter, which corresponds to the outer diameter of the tube 27, although it may be slightly larger or smaller in diameter. Upon expansion by either internal pressure or manipulation of tube 27 and guide wire 25, valve member 28 expands radially to a diameter represented by the arrow 45 in FIG. 3. That expanded diameter is preferably at least equal to the inner diameter of the inner tube 15 of FIG. 1 or at least the inner diameter of segment 40 of director 38 of FIG. 2. With regard to FIG. 2, director 38 may be generally tubular along a significant portion of its length, in which case valve member 28 may also cooperate with portions of director 38 outside segment 40 for control of fluid flow between the interior of the catheter and the patient's body.

FIGS. 4 and 5 represent an alternative embodiment to the guide wire assembly of FIGS. 1–3 and is illustrated in cooperation with a catheter shaft/balloon assembly as illustrated in FIG. 1. The guide wire 25 of FIGS. 4 and 5 may be of conventional design and construction (or any convenient alternative configuration) while the tube 27 may be as illustrated in the guide wire assembly construction illustrated in FIGS. 1–3. The guide wire assembly of FIGS. 4 and 5 differs from that of FIGS. 1–3 principally in the valve member is a hemispherical resilient member 46 which corresponds generally to terminal portion 29 of valve member 28 of FIGS. 1–3.

As in the embodiment of FIGS. 1–3, valve member 46 is connected to tube 27 at bond 47 and to guide wire 25 at bond 48 to define an internal cavity in fluid communication with the interior of tube 27. Accordingly, valve member 46 may be expanded radially by internal pressure via the interior of tube 27 or by manipulation between guide wire 25 and tube 27. That radial expansion is illustrated in FIG. 5, in which an arrow 49 designates an expansion to a diameter at least equal to the diameter of the structure with which valve member 46 is intended to cooperate. In the embodiment of FIG. 4, the diameter is the inner diameter of inner tube 15, while in the embodiment of FIG. 2, it is the diameter of segment 40 (or the inner diameter of a tubular portion of director 38, if different from the inner diameter of segment 40).

Obviously, many modifications and variations of the present invention are possible in light of the above teachings. For example, the guide wire assembly embodiment illustrated in FIG. 3 includes valve member 28 formed as an elongated tubular member having an hemispherical terminus. The length of the tubular member is variable within the scope of the present invention, while the terminus may be hemispherical or of another configuration consistent with the teachings herein. Also the balloon assemblies of the embodiments of FIGS. 1 and 4 include a distal segment 50 with which either of the illustrated embodiments of the guide wire assembly may cooperate. A dilatation catheter assembly in accordance with the present invention may be formed from a guide wire assembly consistent with the teachings herein and any known or desirable "innerless" balloon catheter construction. In addition, the lengths of the elements 10, 13 and 15 may be varied. Finally, the guide wire need not extend through the entire length of tube 27, but instead may be terminated within the end of tube 27 and affixed thereto to extend through the valve member 28 as shown in FIG. 6. It is therefore to be understood that, within the scope of the appended claims, the invention may be practiced otherwise than is specifically described.

What is claimed is:

1. In an angioplasty balloon catheter assembly of a type in which a balloon is carried at a distal end of a catheter shaft, the catheter assembly including a guide wire, the catheter shaft including an inflation lumen by which the balloon is inflated and deflated, and having a guide wire passage communicating with the inflation lumen and extending through the balloon, so that the guide wire can extend through the catheter shaft through the guide wire passage and out a distal end of the balloon; the improvement comprising:

radially expandable valve means carried by the guide wire near a distal end of the guide wire for selectively blocking, at least partially, the guide wire passage during balloon inflation and deflation when in an expanded state, and permitting sliding movement of the guide wire in the guide wire passage when in a non-expanded state, said guide wire including a continuous tube which extends axially over a substantial portion of the length of said guide wire, the radially expandable valve means being operably connected between said tube and the guide wire.

2. The balloon catheter of claim 1 wherein the valve means includes means selectively deformable by internal pressure.

3. The balloon catheter of claim 1, in which the valve means comprises:

said tube positioned over the guide wire with the guide wire extending from a distal end of the tube; and a selectively radially expandable valve member connected to the distal end of the tube.

4. The balloon catheter of claim 3 wherein the expandable valve member is deformable by internal pressure and by manipulation of the tube and guide wire.

5. The balloon catheter of claim 3 wherein said expandable valve means includes means selectively deformable by manipulation of the tube and guide wire.

6. The balloon catheter of claim 3 wherein the valve member has an outer diameter generally corresponding to an outer diameter of the tube, the valve member being selectively expandable beyond the outer diameter of the tube.

7. The balloon catheter of claim 6 wherein said valve member is expandable by internal pressure.

8. The balloon catheter of claim 6 wherein said valve member is expandable by internal pressure and by manipulation of said tube and guide wire.

9. A balloon catheter assembly comprising:

a guide wire having a tube which extends axially over a substantial portion of the length of said guide wire;

a shaft having a proximal end, a distal end, and a lumen which extends between the proximal end and the distal end;

a balloon carried at the distal end of the shaft and means for fluid communication between the interior of said balloon and the lumen proximal to the distal end of said shaft to permit inflation and deflation of the balloon; and radially expandable valve means, carried by the guide wire near a distal end of the guide wire, for selectively blocking fluid flow through the lumen distal of said means for fluid communication, wherein said valve means is connected between said tube and said guide wire.

10. The balloon catheter assembly of claim 9 wherein the valve means comprises a flexible member for positioning within the lumen proximal the distal end of the shaft and means for causing radial expansion of the flexible member to restrict fluid flow through the lumen proximal the distal end of the shaft.

11. The balloon catheter assembly of claim 10 wherein the means for causing radial expansion includes a fluid passage defined by an annular space between said tube and said guide wire through which fluid under pressure can be delivered to cause expansion of the flexible member.

12. The balloon catheter assembly of claim 11 wherein the flexible member has a proximal end connected to a distal end of the tube and a distal end connected to the guide wire.

13. The balloon catheter assembly of claim 10 wherein said tube which extends over said guide wire is axially movable with respect to the guide wire, and wherein the flexible member is connected between the tube and the guide wire so that relative axial movement of the tube with respect to the guide wire in a first direction causes radial expansion of the flexible member and in a second direction causes radial contraction of the flexible member.

14. In an angioplasty balloon catheter assembly of a type in which a balloon is carried at a distal end of a catheter shaft, the catheter assembly including a guide wire, the catheter shaft including an inflation lumen by which the balloon is inflated and deflated, and having a guide wire passage communicating with the inflation lumen and extending through the balloon, so that the guide wire can extend through the catheter shaft through the guide wire passage and out a distal end of the balloon; the improvement comprising:

radially expandable valve means carried by the guide wire near a distal end of the guide wire for selectively blocking, at least partially, the guide wire passage during balloon inflation and deflation when in an expanded state, and permitting sliding movement of the guide wire in the guide wire passage when in a non-expanded state, the radially expandable valve means being connected to the guide wire only at its distal end.

15. The balloon catheter of claim 14 wherein the valve means includes means selectively deformable by internal pressure.

16. The balloon catheter of claim 14, in which the valve means comprises:

a tube positioned over the guide wire with the guide wire extending from a distal end of the tube; and a selectively radially expandable valve member carried at the distal end of the tube.

17. The balloon catheter of claim 16 wherein the expandable valve member is deformable by internal pressure and by manipulation of the tube and guide wire.

18. The balloon catheter of claim 16 wherein said expandable valve means includes means selectively deformable by manipulation of the tube and guide wire.

19. The balloon catheter of claim 16 wherein the valve member has an outer diameter generally corresponding to an outer diameter of the tube, the valve member being selectively expandable beyond the outer diameter of the tube.

20. The balloon catheter of claim 19 wherein said valve member is expandable by internal pressure.

* * * * *